US00PP31712P2

(12) United States Plant Patent
Kordes

(10) Patent No.: US PP31,712 P2
(45) Date of Patent: May 5, 2020

(54) MINIATURE ROSE PLANT NAMED 'KORAROMA08'

(50) Latin Name: *Rosa hybrida*
Varietal Denomination: KORaroma08

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 16/350,310

(22) Filed: Oct. 31, 2018

(30) Foreign Application Priority Data

Oct. 18, 2018 (QZ) ..... PBR 2018/2621

(51) Int. Cl.
*A01H 5/02* (2018.01)
*A01H 6/74* (2018.01)

(52) U.S. Cl.
USPC ..... Plt./117
CPC ..... *A01H 6/749* (2018.05)

(58) Field of Classification Search
USPC ..... Plt./117
CPC ..... A01H 6/749; A01H 5/02
See application file for complete search history.

*Primary Examiner* — Keith O. Robinson
(74) *Attorney, Agent, or Firm* — Buchanan Ingersoll & Rooney PC

(57) ABSTRACT

A new and distinct variety of miniature rose plant, herein referred to by its cultivar name, 'KORaroma08', is provided which forms in abundance on a substantially continuous basis attractive, white colored blossoms. The vegetation is vigorous and the growth habit is compact. Attractive ornamental foliage is formed and good disease resistance is displayed. The new variety is particularly well suited for providing distinctive ornamentation in the landscape.

1 Drawing Sheet

Botanical/commercial classification:
Latin name—*Rosa hybrida.*
Common name—Miniature Rose Plant.
Varietal denomination: 'KORaroma08'.

CROSS-REFERENCE TO RELATED APPLICATIONS

This application claims priority to Plant Breeders' Right Application Number 2018/2621, which was filed at Community Plant Variety Office in the European Union on Oct. 18, 2018, the contents of which are hereby incorporated by reference for all purposes.

SUMMARY OF THE INVENTION

The new variety of *Rosa hybrida* Miniature Rose Plant of the present invention was created during 2015 at Offenseth-Sparrieshoop, Germany by artificial pollination wherein two parents were crossed which previously had been studied in the hope that they would contribute the desired characteristics. The female parent (i.e., seed parent) of the new variety was the 'KORaroma07' variety (non-patented). The male parent (i.e., pollen parent) of the new variety was the 'KORaroma02' variety (non-patented).

The parentage can be summarized as follows:

'KORaroma07' x 'KORaroma02'

The seeds resulting from the above pollination were sown and small plants were obtained which were physically and biologically different from each other. Selective study resulted in the identification of a single plant of the new variety.

It was found that the new miniature rose plant of the present invention possesses the following combination of characteristics:

(a) abundantly and substantially continuously forms attractive, white colored blossoms,
(b) exhibits a compact growth habit,
(c) forms vigorous vegetation,
(d) forms attractive ornamental foliage, and
(e) exhibits good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'KORaroma07' variety (i.e., seed parent) exhibits salmon pink colored flowers and a different flower shape from the new variety. Additionally, the 'KORaroma02' variety (i.e., pollen parent) exhibits a weaker fragrance, a different petal structure, and a smaller growth habit than the new variety. Moreover, the new variety can be readily distinguished from non-parental related similar varieties. For example, the 'KORpot068' variety (U.S. Plant Pat. No. 28,499) displays flowers which have less petals and a shorter duration and exhibits a weaker flower fragrance compared to the new variety.

The new variety has been found to undergo asexual propagation in Klein Offenseth-Sparrieshoop, Germany by a number of routes, such as vegetative cuttings. Asexual propagation techniques in Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORaroma08'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Marslev, Denmark while growing indoors on its own roots in 10.5 cm containers.

FIG. 1—illustrates a specimen of a plant displaying floral buds and flowers at varying points of opening.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based upon a one-year old specimen of the new variety, observed during June, while growing in one-gallon container on its own roots in a greenhouse in Cochranville, Pa. Class: Miniature Rose Plant.

Plant:

*Habit*.—Compact and bushy.

*Height*.—Approximately 31.0 cm on average.

*Width*.—Approximately 30.0 cm on average.

Branches:

*Stem color*.—Commonly near Yellow-Green Group 144A.

*Stem texture*.—Glabrous.

*Main stem length*.—Approximately 31.0 cm on average.

*Secondary stem length*.—Approximately 15.0 cm on average.

*Young thorns*.—Amount: moderate, approximately 1 to 2 thorns over a 3.0 cm length of stem. — length: approximately 4.0 mm on average. — width: approximately 1.0 mm at point of attachment on average. — color: commonly near Greyed-Orange Group 167D.

Foliage:

*General appearance*.—Ornamental.

*Young foliage*.—Upper surface color: commonly near Yellow-Green Group 146A, with venation commonly near Greyed-Orange Group 176A. — under surface color: commonly a blend of near Yellow-Green Group 146C and near Greyed-Orange Group 176B, with venation commonly near Greyed-Orange Group 174B only on the midrib.

*Old foliage*.—Upper surface color: commonly near Green Group 137A, with venation commonly near Greyed-Red Group 182A on the midrib. — under surface color: commonly near Green Group 138B, with venation commonly near Green Group 137D.

*Petiole*.—Upper surface: texture is smooth; color is commonly near Green Group 143D. — under surface: texture is mostly smooth with sparse prickles; color is commonly near Green Group 143C.

*Rachis*.—Color: upper surface is commonly near Greyed-Purple Group 183A; under surface is commonly near Grey-Brown Group 199C.

*Stipules*.—Length: approximately 1.5 cm on average. — width: approximately 5.0 mm on average. — margin: entire to erose. — color: upper surface is commonly near Yellow-Green Group 144A with some blending of near Greyed-Red Group 182A along the inner margin; under surface is commonly near Yellow-Green 144B with some blending of near Greyed-Red Group 182A along the inner margin.

*Leaf margin*.—Serrate.

*Glossiness of upper side of leaf*.—Semi-glossy.

Leaflets:

*Number*.—3, 5, and 7.

*Arrangement*.—Odd-pinnate.

*Shape*.—Ovate; apex is acute; and base is rounded.

*Venation pattern*.—Reticulate.

*Texture*.—Upper surface is smooth; under surface is smooth.

*Terminal leaflet*.—Length is approximately 3.5 cm on average; width is approximately 2.4 cm on average.

*Lower leaflets*.—Length is approximately 2.0 cm on average; width is approximately 1.5 cm on average.

*5-leaflet leaf*.—Length is approximately 9.5 cm on average; width is approximately 6.0 cm on average.

Inflorescence:

*Number of flowers*.—About 3 blooms open on average on a plant at once.

*Number of blossoms per stem*.—Typically 1 to 4 blooms per stem on average.

*Peduncle*.—Color: commonly Yellow-Green Group 144A. — diameter: approximately 7.0 mm on average. — length: approximately 3.5 cm on average. — surface texture: glabrous. — strength: strong.

*Sepals*.—Number commonly 5. — upper surface color and texture: covered in short pubescence; color is commonly near Yellow-Green Group 144A. — under surface color and texture: puberulent; color is commonly near Yellow-Green Group 144A. — size: length is approximately 3.0 cm on average; width is approximately 8.0 mm on average. — margin: entire with occasional extensions on two or three sepals measuring approximately 7.0 mm in length and approximately 3.0 mm in width. — shape: lanceolate; apex is acute to aristate; and base is truncate or flat as it joins the receptacle.

*Bud*.—Shape: globular. — size: length is approximately 2.0 cm on average; width is approximately 1.5 cm on average. — color (when opening): commonly near Yellow Group 8B.

*Flower*.—Form: double, cuplike. — shape: roundish. — profile: flat. — height: approximately 2.5 cm on average. — diameter: approximately 6.0 cm on average. — duration: flower lasts on the plant for 20 days on average.

*Fragrance*.—Moderately sweet fragrance.

*Petal*.—Number: approximately 100 on average. drop: average. — length: inner petals are approximately 1.9 cm on average; outer petals are approximately 3.0 cm on average. — width: inner petals are approximately 1.3 cm on average; outer petals are approximately 2.7 cm on average. — margin: entire. — shape: overall shape is broadly obovate;

apex is rounded; and base is cuneate. — texture: upper and lower surfaces are glabrous. — basal spot on the inner petal: very small and commonly near Yellow Group 8C. — color with first and fully open: upper surface is commonly near Yellow Group 8C at the point of attachment and the rest of the petal surface is near Yellow Group 8D; under surface is commonly near Yellow Group 8D. — color when fading: upper surface is commonly near Yellow Group 8D at the point of attachment and the rest of the petal surface is near White Group NN155D; under surfaces is commonly near White Group NN155D.

*Petaloids*.—Number: 10 on average per flower. — color: upper surface is commonly near Yellow Group 8C; under surface is commonly near Yellow Group 8C. — length: approximately 1.0 cm on average. — width: approximately 4.0 mm on average. — texture: smooth. — margins: variable, entire to erose. — shape: variable, oblong and mostly curving inward. — apex: round. — base: cuneate.

*Stamen*.—Number: approximately 61 on average. — anthers: number is about 61; color is commonly near is commonly near Orange Group 24A; shape is oval; length is approximately 2.0 mm on average. — filaments: length is approximately 5.0 mm on average; color is commonly near Yellow Group 13A.

*Pistils*.—Arrangement: separate and free. — number: approximately 82. — style: color is commonly mostly near Yellow Group 2C and some exhibiting a small hint of Red Group 40D at the base of the stigma; length is less than 6.0 mm on average. — stigma: color is commonly near Yellow Group 2C; diameter is commonly less than 1.0 mm on average; shape is fan shaped.

*Ovary*.—Length is approximately 3.0 mm on average, width is approximately 1.0 mm on average, color is commonly near White Group NN155A.

*Receptacle*.—Achenes stand on the bottom and wall; diameter is approximately 1.3 cm on average; shape is round; color is commonly near Yellow-Green Group 144A; surface texture is smooth.

*Pollen*.—None observed.

*Hips/seed*.—None observed.

Development:

*Vegetation*.—Vigorous and strong.

*Blooming*.—Abundant, re-blooms well from a trim, and substantially continuous.

*Hardiness*.—Unknown.

*Resistance to diseases*.—Good resistance to *Botrytis* (*Botrytis cinerea*) disease and Powdery Mildew (*Sphaerotheca pannosa*) under normal greenhouse growing conditions in Cochranville, Pa.

Plants of the 'KORaroma08' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) abundantly and substantially continuously forms attractive, white colored blossoms, (b) exhibits a compact growth habit, (c) forms vigorous vegetation, (d) forms attractive ornamental foliage, and (e) exhibits good disease resistance;

substantially as herein shown and described.

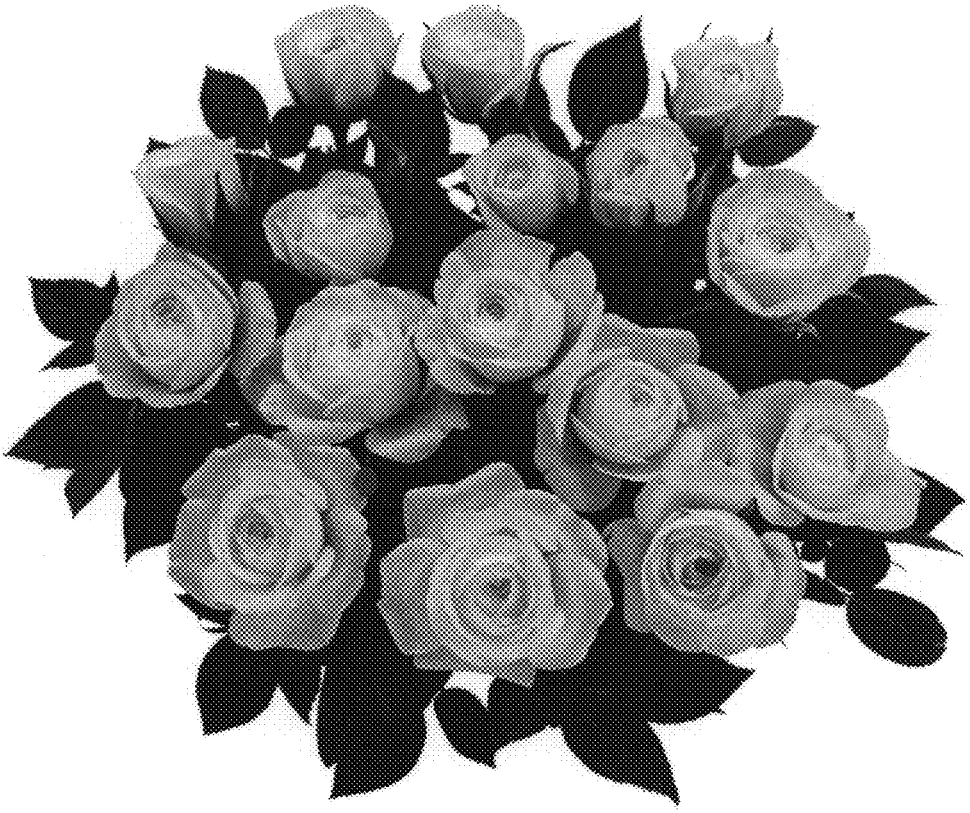

* * * * *